US008293950B2

(12) United States Patent
Jiang et al.

(10) Patent No.: US 8,293,950 B2
(45) Date of Patent: Oct. 23, 2012

(54) METHOD OF PREPARING PENTAERYTHRITOL

(75) Inventors: Yuanhua Jiang, Yichang (CN); Xiaoqin Yang, Yichang (CN); Pingguan Bian, Yichang (CN); Jiaxin Feng, Yichang (CN); Jinjun Dong, Yichang (CN); Huazhong He, Yichang (CN); Yuanhai Li, Yichang (CN); Yexiang Zhang, Yichang (CN); Leguan Huang, Yichang (CN)

(73) Assignee: Hubei Yihua Chemical Industry Co., Ltd., Hubei (CN)

( * ) Notice: Subject to any disclaimer, the term of this patent is extended or adjusted under 35 U.S.C. 154(b) by 644 days.

(21) Appl. No.: 11/993,843

(22) PCT Filed: Mar. 31, 2006

(86) PCT No.: PCT/CN2006/000569
§ 371 (c)(1),
(2), (4) Date: Feb. 22, 2010

(87) PCT Pub. No.: WO2007/000088
PCT Pub. Date: Jan. 4, 2007

(65) Prior Publication Data
US 2010/0152500 A1    Jun. 17, 2010

(30) Foreign Application Priority Data
Jun. 28, 2005 (CN) .......................... 2005 1 0018998

(51) Int. Cl.
*C07C 29/38* (2006.01)
*C07C 31/18* (2006.01)
*C07C 31/24* (2006.01)

(52) U.S. Cl. ....................................... 568/853; 568/854
(58) Field of Classification Search .................. 568/853, 568/854
See application file for complete search history.

(56) References Cited

U.S. PATENT DOCUMENTS

| 2,401,749 | A | * | 6/1946 | Burghardt et al. ............ 568/623 |
| 2,696,507 | A | * | 12/1954 | Cake ............................. 568/854 |
| 2,790,836 | A | * | 4/1957 | Mitchell et al. ............... 568/853 |
| 5,741,956 | A | * | 4/1998 | Eek ............................... 568/853 |

OTHER PUBLICATIONS

Hu, B. et al. (Oct. 2003). "Study on New Synthetic Technology of Pentaerythritol," *Journal of Hubei Polytechnic University* 18(5):4-6. (English abstract attached).
International Search Report mailed Jun. 29, 2006, for PCT Application No. PCT/CN2006/000569 filed Mar. 31, 2006, 6 pages.
Yu, S. (1996). "Production Technology and Development Prospect of Pentaerythritol," *M-Sized Nitrogenous Fertilizer Progress*, pp. 19-20.

* cited by examiner

*Primary Examiner* — Brian J Davis
(74) *Attorney, Agent, or Firm* — Morrison & Foerster LLP

(57) ABSTRACT

A method of preparing monopentaerythritol, dipentaerthritol, and sodium formate through high temperature condensation and cascade recrystallization is disclosed. The method lowers the energy consumption dramatically and improves the cost-effectiveness by carrying out the reaction in a non-low-temperature zone, and thereby avoiding the requirement for refrigeration. The method alleviates the difficulty of separation and improves the product quality by means of cascade separation process, and thereby avoiding the low purity from a single separation. In addition, the mother liquor obtained after each separation step is recycled to the previous step as the recycling liquor, which avoids discharging waste, increases the product yield and lowers raw materials consumption.

7 Claims, No Drawings

METHOD OF PREPARING PENTAERYTHRITOL

CROSS REFERENCE TO RELATED APPLICATIONS

This application is a U.S. National Phase patent application of PCT/CN2006/000569, filed Mar. 31, 2006, claiming priority to China Application Serial No. 200510018998.9, filed Jun. 28, 2005, the contents of which are hereby incorporated by reference in the present disclosure in their entirety.

TECHNICAL FIELD

The present invention relates to a method of preparing pentaerythritol, and more particularly to a method of preparing monopentaerythritol, dipentaerthritol, and byproduct sodium formate by high temperature condensation and cascade recrystallization.

BACKGROUND ART

Pentaetythritol is a kind of polyalcohol, widely used in synthetic resin, plasticizer, lubricating oil, explosive, and so on. It is suitable for use in coating furniture and walls for its good dumb light property. There is a large and increasing demand, especially for high quality (concentration is more than 98%) pentaerythritol. Abroad companies have monopolized the product in this field.

At present methods for preparing pentaerythritol is: reacting formaldehyde with acetaldehyde under alkaline condition into pentaerythritol and formate corresponding to the base, isolating and purifying further. The greatest defect of the method is the production of a large amount of byproducts, and the reaction condition is hard to control. For example, the more the formaldehyde is used compared with acetaldehyde, the more the methylal from pentaerythritol is created; when the amount of formaldehyde is reduced compare with acetaldehyde, the amount of byproducts such as dipentaerythritol, tripentaerythritol and polypentaerythritol is increased. Also, under alkaline condition, the redox reaction will take place between formaldehydes, thereby producing methanol and formate, and the higher the reaction temperature and the concentration of formaldehyde, and the more byproducts are produced. If the reaction temperature is too high, formaldehyde will be glycating to form glucide. Reactions also take place between acetaldehydes and cause the formation of impurities such as β-hydroxyl butyraldehyde.

The reaction of pentaerythritol is under study in the world. For example, UK Patent GB958654 explains the impact on the reaction caused by different reaction temperatures, reaction times and excess formaldehyde. It also discloses a conjunction method for several steps. China Patent CN 1165804A discloses a batch feeding manner, which controls impurities by varying the feeding rate into the reactor. As a result the yield of monopentaerythritol according to this patent is increased compared with continuous production, but the objections are also obvious: (1) reaction temperature is hard to control due to reaction heat concentrated in latter stage when performing the reaction in two stages, which results in partial overheating so as to increase side reactions; (2) yield of monopentaerythritol is decreased due to reacting in one-stage process with adding a mount of acetaldehyde to reduce the ratio of formaldehyde/acetaldehyde; (3) energy consumption is increased by refrigeration to keep low temperature in the first reaction stage to avoid the volatilization loss of acetaldehyde caused by reverse reaction of intermediate from acetaldehyde and formaldehyde. Another China Patent CN1097004 also discloses a condensation process with high-low temperature and low reactants ratio, and an isolation method to obtain monopentaerythritol, dipentaerythritol and tripentaerythritol by liquid accelerator. However, it is hard to obtain high quality monopentaerythritol, dipentaerythritol and tripentaerythritol products from this patent for the same reasons discussed above with respect to CN1165804A.

DISCLOSURE OF THE INVENTION

Technical Problem

The objective of the present invention is to provide a method for preparing monopentaerythritol, dipentaerythritol and sodium formate with low cost, high yield, less byproducts, simple procedures for isolating and purifying the products.

Technical Solution

To achieve the above objective, a method for preparing monopentaerythritol, dipentaerythritol and sodium formate through high temperature condensation and cascade recrystallization is provided in the invention, which comprises the steps of:

(a) condensation reaction: add 15-50% (w/v) of alkaline solution and 60-99% (w/v) of acetaldehyde solution to 10-25% (w/v) of formaldehyde aqueous solution under the initial temperature of 25-45° C. with stirring to obtain the solution with formaldehyde:acetaldehyde:alkaline=4.2-10.2:1:1.05-1.25 (mol), wherein alkaline is added 2-10 minutes before acetaldehyde, take away the reaction heat by coil, jacket and heat exchanger synchronously, maintain reacting 30-100 minutes, control the final reaction temperature of 45-70° C., reaction pressure of 0-0.2 Mpa. After reaction, neutralize the solution to pH=5.5-6.5 with formic acid, then obtain the reaction solution;

(b) monopentaerythritol separation: mix the reaction solution after dealdehydeization and dealcoholization with centrifuged pentaerythritol wash water, then concentrate to have a specific gravity of 1.25-1.28, crystallize and centrifuge to obtain 90-95% of pentaerythritol crude product, and the mother liquor from centrifuging is enter to the next separation process; thereafter add water to dissolve pentaerythritol crude product with heating, then recrystallize, centrifuge, dry and obtain monopentaetythritol.

The method according to the present invention also can comprise the following steps after monopentaerythritol separation:

(c) dipentaerythritol separation: subside the above said mother liquor from monopentaeryth separation, filter supernatant of the above said mother liquor, thereafter the filtrate proceed to succedent separation process, add water to filter residue and heat to 95° C. to dissolve the residue, recrystallize, dry and obtain dipentaerythritol;

(d) sodium formate separation: evaporate/concentrate the filtrate of step (c), keep temperature at 85-110° C., centrifuge when specific gravity reach to 1.3, obtain sodium formate.

The alkaline solution in step (a) is preferably NaOH solution.

The molar ratio among formaldehyde, acetaldehyde and alkaline in step (a) is preferably formaldehyde:acetaldehyde:alkaline=6.5-7.8:1:1.15-1.2.

The initial reaction temperature in step (a) is preferably 30-45° C.; the final reaction temperature is preferably 55-60° C.

Dilute the sodium formate mother liquor from step (d) to 1/3 time with water, heat the diluted mother liquor to 90-100° C., recrystallize to recover pentaerythritol in the solution, thereafter, the obtained mother liquor proceed the step (d) to recover sodium formate.

The concentration of monopentaerythritol obtained from step (b) of the present invention is 95-99%; the concentration of sodium formate obtained from step (d) is 96-99%.

Advantageous Effects

A method of preparing pentaerythritol according to the present invention is performed by combining high temperature condensation with cascade recrystallization separation. The method lowers the energy consumption dramatically and improves the cost-effectiveness by carrying out the reaction in a non-low-temperature zone, and thereby avoiding the requirement for refrigeration. The method alleviates the difficulty of separation and improves the product quality by means of cascade separation process, and thereby avoiding the low purity from a single separation. In addition, the mother liquor obtained after each separation step is recycled to the previous step as the recycling liquor, which avoids discharging waste, increases the product yield and lowers raw materials consumption.

MODE OF CARRYING OUT THE INVENTION

Hereinafter, preferred embodiments of the present invention will be described in detail. Such examples have been provided to illustrate the present invention more clearly, but do not limit the scope of the present invention.

Example 1

The reaction solution with formaldehyde:acetaldehyde:alkaline=5.0:1:1.2 was prepared by dropping alkaline solution (32%) into the formaldehyde solution (12%) for 3 minutes after the pressure was kept at 0.2 Mpa by $N_2$ and the initial temperature was 45° C., then adding acetaldehyde solution (99%) in 80 minutes, and keeping the final temperature at 65° C. during the feeding by cycling cooling water. Thereafter, the solution was neutralized to pH=6 with formic acid, the redundant formaldehyde and methanol was removed, a crystallization solution was obtained by evaporation concentration, and then pentaerythritol containing 91% monopentaerythritol was obtained with a single pass yield of 94.2%. Monopentaerythritol (98.3%) product was obtained by recrystallized the above pentaerythritol. The centrifuged mother liquor was filtered, and the filter residue was cascade dissolved-crystallized twice to obtain dipentaerythritol (93.3%). Crude sodium formate was obtained by concentrating and crystallizing the filtrate. The filtrate therefrom was diluted to 1/3 time by water, then heated to dissolve, crystallized and centrifuged to obtain pentaerythritol. The mother liquor after obtaining pentaerythritol was returned to recover crude sodium formate again. The crude sodium formate was recrystallized to obtained sodium formate product with concentration of 96.5%.

Example 2

The reaction solution with formaldehyde:acetaldehyde:alkaline=6.0:1:1.1 was prepared by dropping alkaline solution (18%) into the formaldehyde solution (18%) for 3 minutes after the pressure was kept at 0.15 Mpa by $N_2$ and the initial temperature was 26° C., then adding acetaldehyde solution (80%) for 60 minutes, and keeping the final temperature at 70° C. during the feeding by cycling cooling water. Thereafter, the solution was neutralized to pH=6.4 with formic acid, the redundant formaldehyde and methanol was removed, a crystallization solution was obtained by evaporative concentration, then pentaerythritol containing 91.5% monopentaerythritol was obtained with a single pass yield of 93%. Monopentaerythritol (98.6%) product was obtained by recrystallizing the above pentaerythritol. The centrifuged mother liquor was filtered, and the filter residue was cascade dissolved-crystallized twice to obtain dipentaerythritol (92.5%). Crude sodium formate was obtained by concentrating and crystallizing the filtrate. The filtrate therefrom was diluted to 1/3 time by water, then heated to dissolve, crystallized and centrifuged to obtain pentaerythritol. The mother liquor after obtaining pentaerythritol was returned to recover crude sodium formate again. The crude sodium formate was recrystallized to obtained sodium formate product with concentration of 97.7%. Centrifuged mother liquor in every step was recycled to keep balance.

Example 3

The reaction solution with formaldehyde:acetaldehyde:alkaline=7.7:1:1.06 was prepared by dropping alkaline solution (45%) into the formaldehyde solution (20%) for 2 minutes after the pressure was kept at 0.1 Mpa by $N_2$ and the initial temperature was 45° C., then adding acetaldehyde solution (89%) for 40 minutes, and keeping the final temperature at 60° C. during the feeding by cycling cooling water. Thereafter, the solution was neutralized to pH=6.2 with formic acid, the redundant formaldehyde and methanol was removed, a crystallization solution was obtained by evaporative concentration, then pentaerythritol containing 93% monopentaerythritol was obtained with a single pass yield of 93.5%. Monopentaerythritol (99.3%) product was obtained by recrystallizing the above pentaerythritol. The centrifuged mother liquor was filtered, and the filtered residue was cascade dissolved-crystallized twice to obtain dipentaerythritol (91%). Crude sodium formate was obtained by concentrating and crystallizing the filtrate. The filtrate therefrom was diluted to 1/3 time by water, then heated to dissolve, crystallized and centrifuged to obtain pentaerythritol. The mother liquor after obtaining pentaerythritol was returned to recover crude sodium formate again. The crude sodium formate was recrystallized to obtained sodium formate product with concentration of 98.6%. Centrifuged mother liquor in every step was recycled to keep balance.

Table of Product Yield

|  | Example 1 | Example 2 | Example 3 |
|---|---|---|---|
| Yield of monopentaerythritol % | 87.4 | 87.8 | 88.5 |
| Yield of dipentaerythritol % | 5 | 3.3 | 3 |
| Yield of sodium formate % | 99.7 | 99.9 | 100.1 |
| Yield calculated by acetaldehyde % | 92.4 | 91.1 | 91.5 |

Comparative Example

Formaldehyde solution (22%) was added to the reactor with stirrer and cooling system, then NaOH solution (16%) and pure acetaldehyde were added to the reactor simultaneously but separately to keep the pH in the range of 10-11, to ensure the addition of half of the total reactants in 25 minutes at the feeding flow rate, while keeping the reaction temperature at 25° C. Thereafter, the flow rate was varied to add the half of the remaining reactants in 25 minutes and the temperature increased to 35° C. The remaining amount of the reactants was added in 35 minutes and the temperature during the feeding was kept no higher than 45° C. The molar ratio of the reactants fed into the reactor was $CH_2O/NaOH/AcH=5.4:1.12:1$. After feeding, the mixture was kept at 45° C. for 10 minutes, acidified to pH5.5 with formic acid, and then sent to buffer tank. The reaction continued in the buffer tank, and then the volatile compound was removed by evaporation, and concentrated, filtered, hydrolyzed, purified and crystallized according to the above said method.

The yield calculated by acetaldehyde was 80.3%.

The invention claimed is:

1. A method for preparing pentaerythritol, the method comprising:
   (a) a condensation reaction comprising:
   adding 15-50% (w/v) of alkaline solution and 60-99% (w/v) of acetaldehyde solution to 10-25% (w/v) of formaldehyde aqueous solution under an initial temperature of 25-45° C. with stirring to obtain a solution of formaldehyde, acetaldehyde and alkaline at a molar ratio of 4.2-10.2 to 1 to 1.05-1.25, and reacting the solution for 30-100 minutes at a final reaction temperature of 45-70° C. and a reaction pressure of 0-0.2 Mpa; and
   after the reaction, neutralizing the solution to a pH of 5.5-6.5 with formic acid to obtain a neutralized solution; and
   (b) a monopentaerythritol separation comprising:
   removing aldehyde and alcohol present in the neutralized solution of step (a) to form a pentaerythritol solution;
   concentrating the pentaerythritol solution to a specific gravity of 1.25-1.28;
   crystallizing and centrifuging the concentrated pentaerythritol solution to obtain 90-95% of pentaerythritol crude product and a mother liquor;
   isolating the mother liquor for use in a further separation process;
   adding water to dissolve the pentaerythritol crude product with heating; and then
   recrystallizing, centrifuging, drying and obtaining monopentaerythritol from the pentaerythritol crude product.

2. The method according to claim 1, wherein the further separation process in step (b) is characterized by the following steps:
   (c) dipentaerythritol separation comprising:
   allowing the isolated mother liquor in step (b) to settle;
   filtering the settled mother liquor to obtain a filter residue and a filtrate;
   adding water to the filter residue and heating to 95° C. to dissolve the filter residue; and
   recrystallizing, drying and obtaining dipentaerythritol from the heated filter residue; and
   (d) pentaerythritol and sodium formate separation comprising:
   evaporatively concentrating the filtrate of step (c);
   at a temperature of 85-110° C. to a specific gravity of 1.3; and
   obtaining a mother liquor comprising pentaerythritol and sodium formate.

3. The method according to claim 1, characterized in that said alkaline solution in step (a) is a 30%-50% NaOH solution.

4. The method according to claim 1, characterized in that the said alkaline solution in step (a) is added 2-10 minutes before the acetaldehyde, and the reaction heat is removed by using a coil, jacket and heat exchanger.

5. The method according to claim 2, further comprising recovering pentaerythritol and sodium formate from the mother liquor of step (d) by:
   diluting the mother liquor of step (d) by 1/3 with water;
   heating the diluted mother liquor to 90-100° C.;
   crystallizing and isolating the pentaerythritol from the heated mother liquor to yield a residual sodium formate mother liquor; and
   recovering sodium formate from the residual sodium formate mother liquor.

6. The method according to claim 1, characterized in that the molar ratio among formaldehyde, acetaldehyde and alkaline in step (a) is 6.5-7.8 to 1 to 1.15-1.2.

7. The method according to claim 1, characterized in that the initial reaction temperature in step (a) is 30-45° C., and the final reaction temperature is 55-60° C.

* * * * *